United States Patent
Grajcar

(10) Patent No.: US 10,455,819 B2
(45) Date of Patent: Oct. 29, 2019

(54) METHODS FOR CONTROLLING SEX OF OVIPAROUS EMBRYOS USING LIGHT SOURCES

(71) Applicant: SIGNIFY NORTH AMERICA CORPORATION, Somerset, NJ (US)

(72) Inventor: Zdenko Grajcar, Crystal, MN (US)

(73) Assignee: SIGNIFY NORTH AMERICA CORPORATION, Somerset, NJ (US)

( * ) Notice: Subject to any disclaimer, the term of this patent is extended or adjusted under 35 U.S.C. 154(b) by 330 days.

(21) Appl. No.: 15/052,021

(22) Filed: Feb. 24, 2016

(65) Prior Publication Data

US 2016/0183499 A1   Jun. 30, 2016

Related U.S. Application Data

(63) Continuation-in-part of application No. 14/103,798, filed on Dec. 11, 2013.

(Continued)

(51) Int. Cl.
*A01K 41/02* (2006.01)
*A01K 45/00* (2006.01)
(Continued)

(52) U.S. Cl.
CPC .............. *A01K 41/02* (2013.01); *A01K 41/00* (2013.01); *A01K 45/007* (2013.01); *A01K 61/17* (2017.01); *A01K 67/02* (2013.01)

(58) Field of Classification Search
CPC ....... A01K 61/00; A01K 67/02; A01K 67/005
(Continued)

(56) References Cited

U.S. PATENT DOCUMENTS 798,697 A    9/1905   Perkins
1,707,539 A  4/1929   Propp
(Continued)

FOREIGN PATENT DOCUMENTS

GB   2271497 A    4/1994
JP   2009-125012 A   6/2009
(Continued)

OTHER PUBLICATIONS

Final Office Action dated Mar. 31, 2017, issued in U.S. Appl. No. 14/103,798.

(Continued)

*Primary Examiner* — Tien Q Dinh
*Assistant Examiner* — Ebony E Evans

(57) ABSTRACT

The sex of embryos in eggs is influenced or controlled through the application of light having selected wavelengths in order to promote the development of embryos of a selected sex. An incubating device is provided having an interior cavity that can be sealed from an outside, and having a plurality of lighting elements disposed on each of a plurality of trays disposed in the interior cavity. Eggs are disposed on the trays, and pre-determined environmental conditions are applied to the interior cavity to promote hatching of the eggs. Concurrently with the application of the environmental conditions, the eggs are irradiated according to pre-determined lighting conditions. The lighting conditions include applying light having wavelengths substantially concentrated in selected ranges, such as light wavelengths within the 390-419 nm, 410-450 nm, 420-450 nm, 450-495 nm, or other narrow range.

17 Claims, 5 Drawing Sheets

Related U.S. Application Data

(60) Provisional application No. 61/735,786, filed on Dec. 11, 2012, provisional application No. 61/746,475, filed on Dec. 27, 2012, provisional application No. 61/759,536, filed on Feb. 1, 2013, provisional application No. 61/802,826, filed on Mar. 18, 2013, provisional application No. 61/813,905, filed on Apr. 19, 2013, provisional application No. 61/845,466, filed on Jul. 12, 2013.

(51) Int. Cl.
    *A01K 41/00*     (2006.01)
    *A01K 67/02*     (2006.01)
    *A01K 61/17*     (2017.01)

(58) Field of Classification Search
    USPC .................. 119/6.6, 6.8, 306, 50.7, 318
    See application file for complete search history.

(56) References Cited

U.S. PATENT DOCUMENTS

| | | | | |
|---|---|---|---|---|
| 1,846,756 | A | 2/1932 | Robbins | |
| 1,943,575 | A | 1/1934 | Abendroth | |
| 1,977,905 | A | 10/1934 | Bohmker | |
| 2,403,705 | A | 7/1946 | Bramson | |
| 2,612,863 | A * | 10/1952 | Wade, Sr. | A01K 31/19 119/301 |
| 2,734,482 | A | 2/1956 | Seltzer | |
| 2,928,211 | A | 3/1960 | Martin | |
| 2,980,059 | A * | 4/1961 | Bradley | A01K 41/00 119/318 |
| 3,006,320 | A | 10/1961 | Bailey | |
| 3,028,208 | A | 4/1962 | Sharpe | |
| 3,147,738 | A | 9/1964 | Theilig | |
| 3,352,684 | A | 11/1967 | Gard | |
| 3,529,379 | A | 9/1970 | Ware | |
| 3,741,158 | A | 6/1973 | Moe, Jr. et al. | |
| 3,797,172 | A | 3/1974 | Cannon | |
| 4,045,911 | A | 9/1977 | Ware | |
| 4,215,651 | A | 8/1980 | Pearce | |
| 4,250,666 | A | 2/1981 | Rakestraw | |
| 4,378,758 | A * | 4/1983 | Coleman | A01K 41/00 119/300 |
| 4,625,728 | A * | 12/1986 | Schonberg | A01G 7/00 119/6.8 |
| 4,640,033 | A | 2/1987 | Bulger | |
| 4,765,337 | A | 8/1988 | Schonberg | |
| 4,803,949 | A * | 2/1989 | Kiyokawa | A01K 63/06 119/233 |
| 5,013,906 | A | 5/1991 | Miyakawa et al. | |
| 5,090,617 | A | 2/1992 | Swan et al. | |
| 5,173,737 | A | 12/1992 | Mitchell et al. | |
| 5,251,574 | A | 10/1993 | Foster et al. | |
| 5,297,863 | A | 3/1994 | Richardson et al. | |
| 5,575,237 | A | 11/1996 | Ferguson | |
| 5,690,415 | A | 11/1997 | Krehl | |
| 5,745,228 | A * | 4/1998 | Hebrank | A01K 45/007 250/341.1 |
| 5,814,078 | A * | 9/1998 | Zhou | A61N 1/40 607/1 |
| 6,015,713 | A | 1/2000 | Wright, Jr. et al. | |
| 6,152,575 | A | 11/2000 | Montanino | |
| 6,312,139 | B1 | 11/2001 | Baker et al. | |
| 6,523,976 | B1 | 2/2003 | Turnbull et al. | |
| 6,584,935 | B2 | 7/2003 | Zohar et al. | |
| 6,680,200 | B2 * | 1/2004 | Everett | A01G 7/04 435/284.1 |
| 6,766,767 | B2 | 7/2004 | El Halawani et al. | |
| 6,789,500 | B2 | 9/2004 | Rozenboim | |
| 6,805,465 | B2 | 10/2004 | Chen | |
| 6,921,182 | B2 * | 7/2005 | Anderson, Jr. | A01G 7/045 362/230 |
| 6,953,266 | B1 | 10/2005 | Ver Hage et al. | |
| 6,965,205 | B2 * | 11/2005 | Piepgras | H05B 33/0857 315/292 |
| 7,032,540 | B2 | 4/2006 | Bonner et al. | |
| 7,131,397 | B2 | 11/2006 | El Halawani et al. | |
| 7,221,104 | B2 * | 5/2007 | Lys | A61N 5/0616 315/291 |
| 7,287,870 | B1 | 10/2007 | Knoch | |
| 7,441,916 | B2 | 10/2008 | Masuyama et al. | |
| 7,473,008 | B2 | 1/2009 | Crabb et al. | |
| 7,482,764 | B2 | 1/2009 | Morgan et al. | |
| 7,588,340 | B2 | 9/2009 | Bauer et al. | |
| 7,806,543 | B2 | 10/2010 | Swofford et al. | |
| 7,950,817 | B2 | 5/2011 | Zulim et al. | |
| 8,069,819 | B2 | 12/2011 | Huisinga et al. | |
| 8,230,815 | B2 | 7/2012 | Fredricks | |
| 8,272,352 | B2 | 9/2012 | Hendel | |
| 8,277,087 | B2 | 10/2012 | Chien | |
| 8,373,363 | B2 | 2/2013 | Grajcar | |
| 8,468,976 | B2 * | 6/2013 | Kakimi | A01K 31/18 119/174 |
| 8,643,308 | B2 | 2/2014 | Grajcar | |
| 8,889,662 | B2 | 11/2014 | Navara | |
| 9,137,874 | B2 | 9/2015 | Maxik et al. | |
| 9,526,215 | B2 * | 12/2016 | Suntych | A01G 7/045 |
| 9,560,837 | B1 * | 2/2017 | Suntych | A01K 45/00 |
| 9,642,314 | B1 | 5/2017 | Joseph | |
| 9,844,210 | B2 * | 12/2017 | Grajcar | A01K 45/007 |
| 10,015,952 | B2 * | 7/2018 | Adar | A01K 43/00 |
| 2001/0027569 | A1 | 10/2001 | Cantrell et al. | |
| 2002/0014444 | A1 | 2/2002 | Hebrank | |
| 2003/0003437 | A1 | 1/2003 | Rozenboim | |
| 2004/0040515 | A1 | 3/2004 | Taniguchi | |
| 2006/0072318 | A1 | 4/2006 | Witham et al. | |
| 2007/0024843 | A1 * | 2/2007 | Hebrank | G01N 33/08 356/53 |
| 2007/0245973 | A1 | 10/2007 | Huisinga et al. | |
| 2007/0261128 | A1 | 11/2007 | Cantrell et al. | |
| 2007/0275037 | A1 | 11/2007 | Ding et al. | |
| 2008/0047181 | A1 | 2/2008 | Sakai | |
| 2009/0021956 | A1 | 1/2009 | Grobler et al. | |
| 2009/0199780 | A1 | 8/2009 | Hendel | |
| 2010/0186428 | A1 | 7/2010 | Meter | |
| 2010/0306869 | A1 | 12/2010 | Doran et al. | |
| 2011/0000437 | A1 | 1/2011 | Meter | |
| 2011/0094452 | A1 | 4/2011 | Huisinga et al. | |
| 2011/0101883 | A1 | 5/2011 | Grajcar | |
| 2011/0109244 | A1 | 5/2011 | Grajcar | |
| 2011/0210678 | A1 | 9/2011 | Grajcar | |
| 2011/0228515 | A1 | 9/2011 | Grajcar | |
| 2011/0241559 | A1 | 10/2011 | Grajcar | |
| 2011/0273098 | A1 | 11/2011 | Grajcar | |
| 2012/0042829 | A1 | 2/2012 | Hendel | |
| 2012/0186523 | A1 | 7/2012 | Sia | |
| 2012/0186524 | A1 | 7/2012 | Grajcar | |
| 2012/0268918 | A1 | 10/2012 | Grajcar | |
| 2012/0304322 | A1 | 11/2012 | Yamaha et al. | |
| 2013/0092094 | A1 | 4/2013 | Meter | |
| 2013/0104809 | A1 | 5/2013 | Meter | |
| 2013/0152864 | A1 | 6/2013 | Grajcar et al. | |
| 2014/0126174 | A1 | 5/2014 | Grajcar | |
| 2014/0158050 | A1 | 6/2014 | Grajcar | |
| 2014/0159615 | A1 | 6/2014 | Grajcar | |
| 2014/0165468 | A1 | 6/2014 | Roeser et al. | |
| 2015/0122182 | A1 | 5/2015 | Aldana et al. | |
| 2015/0124426 | A1 | 5/2015 | Grajcar | |
| 2015/0136030 | A1 * | 5/2015 | Meissner | A01K 43/00 119/6.8 |
| 2015/0138537 | A1 | 5/2015 | Yamamoto et al. | |
| 2015/0204497 | A1 | 7/2015 | Grajcar | |
| 2015/0223402 | A1 * | 8/2015 | Krijn | A01G 7/045 47/58.1 LS |
| 2015/0230440 | A1 | 8/2015 | Grajcar et al. | |
| 2016/0356465 | A1 | 12/2016 | Polete | |
| 2017/0071166 | A1 | 3/2017 | Grajcar et al. | |
| 2017/0071167 | A1 | 3/2017 | Grajcar et al. | |

(56) References Cited

U.S. PATENT DOCUMENTS

| | | |
|---|---|---|
| 2017/0071168 A1 | 3/2017 | Grajcar et al. |
| 2017/0074464 A1 | 3/2017 | Grajcar et al. |

FOREIGN PATENT DOCUMENTS

| | | |
|---|---|---|
| RU | 2002113424 A | 2/2004 |
| RU | 2225105 C2 | 3/2004 |
| WO | 9413132 A1 | 6/1994 |
| WO | 2011/141559 A1 | 11/2011 |
| WO | 2014093445 A1 | 6/2014 |
| WO | 2014126466 A1 | 8/2014 |
| WO | 2015/017655 A1 | 2/2015 |
| WO | 2015/023178 A1 | 2/2015 |
| WO | 2015/052626 A1 | 4/2015 |
| WO | 2016053088 A1 | 4/2016 |

OTHER PUBLICATIONS

Non-Final Office Action dated May 4, 2017, issued in U.S. Appl. No. 14/696,267.
Final Office Action dated Apr. 11, 2017, issued in U.S. Appl. No. 14/992,935.
Extended European Search Report dated Jun. 29, 2016, issued in European Patent Application No. 13862077.8.
U. Narendra et al. "Sex-specific Gene Regulation the Doublesex Dm Motif is a Bipartite DNA-Binding Domain." Journal of Biological Chemistry, vol. 277 No. 45 (2002):pp. 43463-43473.
L. Zhu et al. "Sexual dimorphism in diverse metazoans is regulated by a novel class of intertwined zinc fingers." Genes & Development, vol. 14 No. 14 (2000): 1750-1764.
C.A. Smith et al. "The avian Z-linked gene DMRT1 is required for male sex determination in the chicken." Nature, vol. 461 No. 7261 (2009): pp. 267-271.
H. Masuyama et al. "Dmrt1 mutation causes a male-to-female sex reversal after the sex determination by Dmy in the medaka." Chromosome Research, vol. 20 No. 1 (2012):pp. 163-176.
International Preliminary Report on Patentability and Written Opinion issued in International Patent Application No. PCT/US2013/074308; dated Jun. 16, 2015.
International Search Report and Written Opinion issued in corresponding International Patent Application No. PCT/US2015/027560, dated Jul. 15, 2015.
Pandian et al. "Androgenesis and conservation of fishes" Current Science, Oct. 10, 2003,(Oct. 10, 2003), vol. 85, No. 7, pp. 1-15. entire document.
Moreira De Figueiredo, F. "Control of sexual maturation and growth in Atlantic cod (Gadus morhua) by use of Cold Cathode Light technology," Thesis, Holar University College, Department of Aquaculture and Fish Biology, Apr. 1, 2013, pp. 1-106. Retrieved from the internet:<http://skemman.is/stream/get/1946/16873/39137/1/MSc_ Thesis_Filipe _Figueiredo_Final_version_23-05-3.pdf.> on Jul. 7, 2015 (Jul. 7, 2015). entire document.
Romanoff, A. L. and C. L. Cottrell, 1939. Bioelectric potentials of the hen's egg. Science 90: (2342) 471-472.
Romanoff, A. L., 1943. Stimulating effects of ultraviolet radiation on bioelectric potentials of an avian egg. J. Cell Comp. Physiol. 20: 123-127.
Shutze, J. V., J. K. Lauber, J. Kato and W. Wilson, 1962. Influence of incandescent and coloured light on chick embryos during incubation. Nature (London) 96: 594-595.
Tamimie, H. S. and M. W. Fox, 1967. Effect of continuous and intermittent light exposure on embryonic development of chicken eggs. Comp. Biochem. and Physiol. 20: 793-799.
Isakson, S. T., B. J. Huffman and P. B. Siegel, 1970. Intensities of incandescent light and the development of chick embryos in ovo and in vitro. Comp. Biochem. Physiol. 34: 299-305.
Siegel, P. B., S. T. Isakson, F. N. Coleman and B. J. Huffman, 1969. Photoacceleration of development in chick embryos. Comp. Biochem. Physiol. 28: 753-758.
Cooper, J. B., 1972. Effect of light during incubation on hatchability of turkey eggs. Poultry Sci. 51: 1105-1108.
Walter, J. H. and R. A. Voitle, 1972. Effects of photoperiod during incubation on embryonic and post embryonic development of broilers. Poultry Sci. 51: 1122-1126.
Gold, P. S. and J. Kalb, 1976. Secondry heating of chicken eggs exposed to light during incubation. Poultry Sci. 55: 34-39.
Coleman, M.A. and C. R. McDaniel, 1975. The Effect of Light and Specific Gravity on Embryo weight and Embryonic Mortality Poult. Sci. 54: 1415-142.
Walter, J. H. and R. A. Voitle, 1973. Effect of photoperiod during incubation on embryonic and post embryonic development of quail and chickens. Br. Poultry Sci. 14: 533-540. (Abstract).
U.S. Appl. No. 61/570,552, filed Dec. 14, 2011; 59 pages.
Tamimie, H. S., 1967. Light exposure of incubating eggs and its influence on the growth of chicks. I. Brooding chicks under different light regimes. Comp. Biochem. Physiol. 21: 59-63.
International Search Report issued in PCT/US13/74308 dated Feb. 21, 2014.
Viktor Hamburger and Howard L. Hamilton, "A series of normal stages in the development of the chick embryo," Developmental Dynamics, vol. 195, Issue 4, pp. 231-272, Dec. 1992.
Non-Final Office Action dated Apr. 15, 2015, issued in corresponding U.S. Appl. No. 14/103,798.
Notice of Allowance dated Sep. 30, 2015 issued in corresponding U.S. Appl. No. 14/103,798.
Non-Final Office Action dated Feb. 22, 2016, issued in corresponding U.S. Appl. No. 14/877,881.
Tai, M., et al., "Effect of LED Chromatic Light Sources on Hatching of Broiler Breeder Eggs." Journal of Chinese Society of Animal Science. vol. 37 No. 1. pp. 1-7. 2008; (w/ English translation).
Kettlewell J.R. et al., "Temperature-Dependent Expression of Turtle Dmrt1 Prior to Sexual Differentation". Genesis. 2000: vol. 26: pp. 174-178.
Zhang, L. et al. "Effect of monochromatic light stimuli during embryogenesis on muscular growth, chemical composition, and meat quality of breast muscle in male broilers." Poultry Science. 2012; vol. 91: pp. 1026-1031.
Veterany, L. et al., "The Effect of Light on Chicken Hatching." Scientia Agriculturae Bohemica. 2002; vol. 33 No. 4. pp. 150-152.
Raymond C.S. et al., "Expression of Dmtr1 in the Genital Ridge of Mouse and Chicken Embryos Suggests a Role in Vertebrate Sexual Development." Development Biology. 1999; vol. 215: pp. 208-220.
Seremet, C. et al. "The effects of monochromatic lighting on embryonic development and hatching performance depending on egg shell colour." Avian Biology Research, 2012; vol. 5, No. 3, p. 182. (Abstract).
Tzschentke, B. et al., "Imprinting of body functions by manipulation of incubation temperature and its long-lasting effect on hatchability, performance and health in poultry." Avian Biology Research, 2012; vol. 5, No. 3. p. 182. (Abstract).
Veternany, L. et al., "The Influence of Non-Ionic Radiation on the Chicken Hatching." Journal of Environmental Science and Health (Part A—Toxic/Hazardous Substances & Environmental Engineering. 2002; vol. 37, No. 10: pp. 1849-1854.
Shafey, T.M. et a., "Embryonic Growth, Hatching Time and Hatchability Performance of Meat Breeder Eggs Incubated Under Continuous Green Light." Asian Australasian Journal of Animal Sciences. 2002; vol. 15, No. 12. pp. 1702-1707.
Rozenboim, I. et al., "Effect of Embryonic Photostimulation on the Posthatch Growth of Turkey Poults." Poultry Science. 2003; vol. 82. No. 7. pp. 1181-1187.
Archer, G.S. et al., "The effects of light stimulation during incubation on indicators of stress susceptibility in broilers." Poultry Science. 2013; vol. 92 No. 12. pp. 3103-3108.
Archer, G.S. et al., "Effect of providing light during incubation on the health, productivity, and behavior of broiler chickens." Poultry Science. 2009; vol. 88 No. 1. pp. 29-37.
Decuypere, E. et al., "The Endocrine Interface of Environmental and Egg Factors Affecting Chick Quality." Poultry Science. 2007; vol. 86 No. 5. pp. 1037-1042.
Erwin, W.T. et al., "Response of the Developing Embryo to Light." Poultry Science. 1971; vol. 50 No. 6. pp. 1883-1884.

(56) References Cited

OTHER PUBLICATIONS

Fairchild, B.D. et al., "Photostimulation of Turkey Eggs Accelerates Hatching Times Without Affecting Hatchability, Liver or Heart Growth, or Glycogen Content." Poultry Science. 2000; vol. 79 No. 11. pp. 1627-1631.
Ghatpande, A. et al., "Effect of different intensities of fluorescent light on the early development of chick embryos in ovo." Cellular & Molecular Biology Research. 1994; vol. 41 No. 6. pp. 613-621. (Abstract).
Huth, J.C. et al., "Effects of LED lighting during incubation on layer and broiler hatchability, chick quality, stress susceptibility and post-hatch growth." Poultry Science. 2015; vol. 94. pp. 3052-3058.
Lauber, J.K. "Photoacceleration of Avian Embryogenesis." Comparative Biochemistry and Physiology part A: Physiology. 1975; vol. 51 No. 4: pp. 903-907.
Rogers, L.J. et al., "Light Exposure During Incubation Affects Competitive Behaviour in Domestic Chicks." Applied Animal Behaviour Science. 1989; vol. 23 No. 3: pp. 187-198.
Shutze, J.V., et al. "Influence of incandescent and coloured light on chicken embryos during incubation." Nature. 1962; vol. 196: pp. 594-595.
Siegel, P.B. et al., "Photoacceleration of Development in Chick Embryos." Comparative Biochemistry and Physiology. 1969; vol. 28 No. 2: pp. 753-758.
Gonzalez, A. et al., "Factors Affecting Ostrich Egg Hatchability." Poultry Science. 1999; vol. 78 No. 9: pp. 1257-1262.
Peebles, D.E. et al., "Effects of Dietary Fat and Eggshell Cuticle Removal on Egg Water Loss and Embryo Growth in Broiler Hatching Eggs." Poulltry Science. 1998; vol. 77 No. 10: pp. 1522-1530.
Bednarczyk, M.F. et al., "Influence de l'èclairement de l'embryon de poulet sur le taux d'èclosion, la durèe d'incubation et l'hèmatopoièse." Annales de Recherches Veterinaires, 1984; vol. 15 No. 3: pp. 411-416. (w/ English summary).
Stavar, P. et al., "The Effect of Red and Blue Light Upon the Embryonary Development and the Ratio Between Sexes." Lucrari stiintifice. 1973; vol. 2: pp. 113-126 (w/ English translation).
Non-Final Office Action issued in related U.S. Appl. No. 14/103,798 dated Apr. 15, 2015.
Black, R.G., "Lighting for Finches and Other Caged Birds", Full Spectrum Lights for Birds Article, Parrot-and-Conure-World.com, <http://www.parrot-and-conure-world.com/full-spectrum-lights-for-birds.html., 2016.
Non-Final Office Action dated Sep. 9, 2016, Issued in U.S. Appl. No. 14/103,798.
International Preliminary Report on Patentability and Written Opinion issued in International Patent Application No. PCT/US2015/027560; dated Oct. 25, 2016.
Final Office Action dated Nov. 29, 2016, issued in U.S. Appl. No. 14/877,881.
Non-Final Office Action dated Apr. 6, 2016, issued in U.S. Appl. No. 14/992,935.
Supplemental Notice of Allowance dated Apr. 21, 2016, issued in U.S. Appl. No. 14/103,798.
Final Office Action issued in related U.S. Appl. No. 14/696,267, dated Nov. 2, 2017.
Non-Final Office Action issued in related U.S. Appl. No. 14/877,881, dated Nov. 1, 2017.
Non-Final Office Action issued in related U.S. Appl. No. 14/992,935, dated Nov. 2, 2017.
International Search Report and Written Opinion issued in International Patent Application No. PCT/US2016/51607 dated Jan. 27, 2017.
International Search Report and Written Opinion issued in International Patent Application No. PCT/US2016/51616 dated Feb. 17, 2017.
International Search Report and Written Opinion issued in International Patent Application No. PCT/US2016/51613 dated Dec. 7, 2016.
International Search Report and Written Opinion issued in International Patent Application No. PCT/US2016/51603 dated Feb. 9, 2017.
Torben Ross, "The Chicken Egg Incubator", Nov. 12, 2015.
S. Ozkan et al., "Photoperiodic lighting (16 hours of light: 8 hours of dark) programs during incubation: 2. Effects on early posthatching growth, blood physiology, and production performance in broiler chickens in relation to posthatching lighting programs", 2012 Poultry Science, 91, pp. 2922-2930.
Evalyne Githinji, "Smartphone hatches fresh idea for chicken breeder", Business Daily, Small Enterprise, Sep. 30, 2013.
Hatchtech, Hatchbrood Brooding Control, The Netherlands.
Examination Report dated Jun. 9, 2017 for AU Application No. AU2013359383.
Global Dossier translation of First CN Office Action dated Sep. 2, 2016 for CN Application No. CN2013800644303.
Global Dossier translation of Second CN Office Action dated Jul. 5, 2017 for CN Application No. CN2013800644303.
English Summary translation of JP Office Action dated Sep. 5, 2017 for JP Application No. JP 2015545947.
S. Ozkan et al., "Photoperiodic lighting (16 hours of light: 8 hours of dark) programs during incubation: 1. Effects on growth and circadian physiological traits of embryos and early stress response of broiler chickens", 2012 Poultry Science, 91, pp. 2912-2921.
"International Application Serial No. PCT/US2016/051603, Invitation to Pay Add'l Fees and Partial Search Report dated Dec. 2, 2016", 2 pgs.
"International Application Serial No. PCT/US2016/051607, Invitation to Pay Add'l Fees and Partial Search Report dated Nov. 21, 2016", 2 pgs.
"International Application Serial No. PCT/US2016/051616, Invitation to Pay Add'l Fees and Partial Search Report dated Nov. 21, 2016", 2 pgs.

* cited by examiner

METHODS FOR CONTROLLING SEX OF OVIPAROUS EMBRYOS USING LIGHT SOURCES

CROSS-REFERENCE TO RELATED APPLICATIONS

This application is a continuation in part of U.S. patent application Ser. No. 14/103,798 entitled Method for Controlling Sex of Oviparous Embryos Using Light Sources filed Dec. 11, 2013 to Grajcar that claims priority from U.S. Provisional Patent Application No. 61/735,786, filed on Dec. 11, 2012; U.S. Provisional Patent Application No. 61/746,475, filed on Dec. 27, 2012; U.S. Provisional Patent Application No. 61/759,536filed on Feb. 1, 2013, U.S. Provisional Patent Application No. 61/802,826 filed on Mar. 18, 2013; U.S. Provisional Patent Application No. 61/813,905 filed on Apr. 19, 2013; and U.S. Provisional Patent Application No. 61/845,466 filed on Jul. 12, 2013, all to Grajcar, the disclosures of which are all incorporated herein in their entireties.

TECHNICAL FIELD

This disclosure relates to controlling the sex of avians, fish, or other oviparous animals at the embryonic stage. More specifically, this disclosure is directed to applying selected wavelengths of light and/or electromagnetic radiation to eggs in order to influence the sex of embryos within the eggs.

BACKGROUND

While sex (or gender) in higher vertebrates is determined at fertilization, sex determining genes in chicken become active at a later stage during embryogenesis to induce the formation of testes or ovaries. This has led to the long-standing belief that much of the underlying genetic pathway is conserved through the later stage of embryogenesis. However, comparative studies on sex determination in the chicken embryo have revealed both conserved and divergent elements in the pathway. For example, the gonads of chicken embryos are morphologically indistinguishable between the sexes, and thus "indifferent" or "bipotential," at days 3.5-4.5.

In the poultry and other animal-production markets, including but not limited to chickens, turkeys, and the like, the ability to control or affect the sex of the animals would greatly enhance the production and efficiency of production. For example, in egg laying operations only hens or females are desired. Thus, when a flock of avian is born, only female avians are retained and often male avians are euthanized or otherwise disposed of. Because males and females are born at an approximate 50/50 sex ratio, approximately half of all avian born at such operations are thus lost and unproductive or provide diminished production.

A need thus exists for controlling, promoting, or otherwise influencing the sex of the avians before hatching in order to selectively produce more male or female avians, and thereby increase production and decrease waste and costs. A need also exist for robust cost effective lighting fixtures that can achieve such results.

SUMMARY

The teachings herein alleviate one or more of the above noted problems with established incubation methods, by enabling the sex of embryos in eggs to be influenced or controlled through the application of light having selected wavelengths.

According to one aspect of the disclosure, a method of promoting production of embryos of a selected sex in eggs is provided. The method includes incubating a plurality of fertilized eggs to promote hatching of the eggs, and irradiating the plurality of fertilized eggs with light having a spectrum substantially concentrated within a narrow range of wavelengths while the plurality of fertilized eggs are incubated.

The narrow range of wavelengths may be one of a 410-450 nm wavelength range and a 450-495 nm wavelength range.

The method may further include selecting the narrow range of wavelengths for the spectrum of light irradiating the eggs based on the selected sex of embryos being promoted in the eggs. In one example, the narrow range of wavelengths may be selected to be the 410-450 nm wavelength range when production of female embryos is promoted. In another example, the narrow range of wavelengths may be selected to be the 450-495 nm wavelength range when production of male embryos is promoted.

The plurality of fertilized eggs may be irradiated with light having the spectrum substantially concentrated within the narrow range of wavelengths during the first 6 days of incubation.

The plurality of fertilized eggs may only be irradiated with light having the spectrum substantially concentrated within the narrow range of wavelengths while the plurality of fertilized eggs are incubated. Optionally, the method may thus include shielding the plurality of fertilized eggs from light having a spectrum substantially concentrated outside of the narrow range of wavelengths while the plurality of fertilized eggs are incubated. The irradiating of the eggs may include irradiating the plurality of fertilized eggs with light having an intensity of 3 lumens or less while the plurality of fertilized eggs are incubated.

According to another aspect of the disclosure, an incubating device is provided that includes a body having an interior cavity that can be sealed from an outside of the body, a plurality of trays disposed in the interior cavity and configured to receive eggs for incubation, a plurality of lighting elements disposed on each tray of the plurality of trays and configured to emit light having a spectrum substantially concentrated within a pre-determined narrow wavelength range for irradiating the eggs, and a lighting controller electrically connected to the plurality of lighting elements and configured to activate the lighting elements at a pre-determined lighting intensity and according to a pre-determined schedule to irradiate the eggs with light having a spectrum substantially concentrated within the pre-determined wavelength range and having the pre-determined lighting intensity according to the pre-determined schedule.

The plurality of lighting elements can include a first plurality of lighting elements disposed on each tray of the plurality of trays and configured to emit light having a spectrum substantially concentrated within a first pre-determined wavelength range, and a second plurality of lighting elements disposed on each tray of the plurality of trays and configured to emit light having a spectrum substantially concentrated within a second pre-determined wavelength range different from the first pre-determined wavelength range. The lighting controller can be electrically connected to the first and second pluralities of lighting elements and configured to separately activate the lighting elements of the first and second pluralities of lighting elements with respective lighting intensities and according to respective schedules for irradiating the eggs.

Each tray of the plurality of trays can have an upper surface configured to have the eggs disposed thereon and a lower surface opposite to the upper surface, and the plurality of lighting elements can include lighting elements disposed on the lower surface of at least one tray. The plurality of lighting elements can further include lighting elements disposed on the upper and lower surfaces of at least one tray.

The lighting elements may be configured to emit light with wavelengths substantially concentrated within narrow bands of wavelengths including but not limited to the range of 410-450 nm and/or 450-495 nm.

The lighting elements can be light emitting diodes (LEDs).

The incubating device can include at least one tray actuator mechanically coupled to each of the plurality of trays, and operative to move the trays having the eggs for incubation. Each tray of the plurality of trays may be rotatable about an axis, and the at least one tray actuator may be configured to rotate the trays to cause the trays to tilt in response to a control signal received by the actuator. The device may further include a controller electrically connected to the at least one tray actuator and including the lighting controller, and the controller may be configured to control the operation of the at least one tray actuator and the plurality of lighting elements according to the pre-determined schedule.

The incubating device can further include a magnetic field source disposed in the interior cavity and configured to produce a magnetic flux in the interior cavity for application to the eggs.

According to another aspect of the disclosure, a method includes disposing, in an incubating device having an interior cavity that can be sealed from an outside, a plurality of lighting elements on each of a plurality of trays disposed in the interior cavity and configured to receive eggs for incubation, wherein each lighting element of the plurality of lighting elements is configured to emit light having a spectrum substantially concentrated within a pre-determined narrow range of wavelengths. A plurality of eggs is disposed on each of the plurality of trays having lighting elements disposed thereon, and pre-determined environmental conditions are applied to the interior cavity of the incubating device, wherein the environmental conditions are selected to promote hatching of the plurality of eggs. Pre-determined lighting conditions including lighting having a spectrum substantially concentrated within the pre-determined narrow range of wavelengths are further applied to the interior cavity of the incubating device, wherein the lighting conditions are applied during the application of the environmental conditions selected to promote hatching of the plurality of eggs.

The pre-determined lighting conditions can be selected to promote production of embryos of a selected sex in the eggs, and the narrow range of wavelengths is selected based on the selected sex.

The environmental conditions can be applied according to a pre-determined schedule, and the lighting conditions can be applied according to the same pre-determined schedule.

The lighting elements may be configured to emit light with wavelengths substantially concentrated within ranges 410-450 nm and/or 450-495 nm.

The disposing the plurality of lighting elements on each of the plurality of trays can include disposing, on each tray of the plurality of trays, a first plurality of lighting elements configured to emit light having wavelengths substantially concentrated within a first pre-determined wavelength range, and a second plurality of lighting elements configured to emit light having wavelengths substantially concentrated within a second pre-determined wavelength range different from the first pre-determined wavelength range. The applying pre-determined lighting conditions to the interior cavity of the incubating device can include separately activating the lighting elements of the first and second pluralities of lighting elements with respective lighting intensities and according to respective schedules for irradiating the eggs.

Each tray can have an upper surface configured to have the eggs disposed thereon and a lower surface opposite to the upper surface, and the disposing the plurality of lighting elements on each of the trays can include disposing lighting elements on the lower surface of at least one tray.

The applying pre-determined lighting conditions to the interior cavity of the incubating device can include causing the lighting elements to emit light having an intensity of 3 lumens or less.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1A:
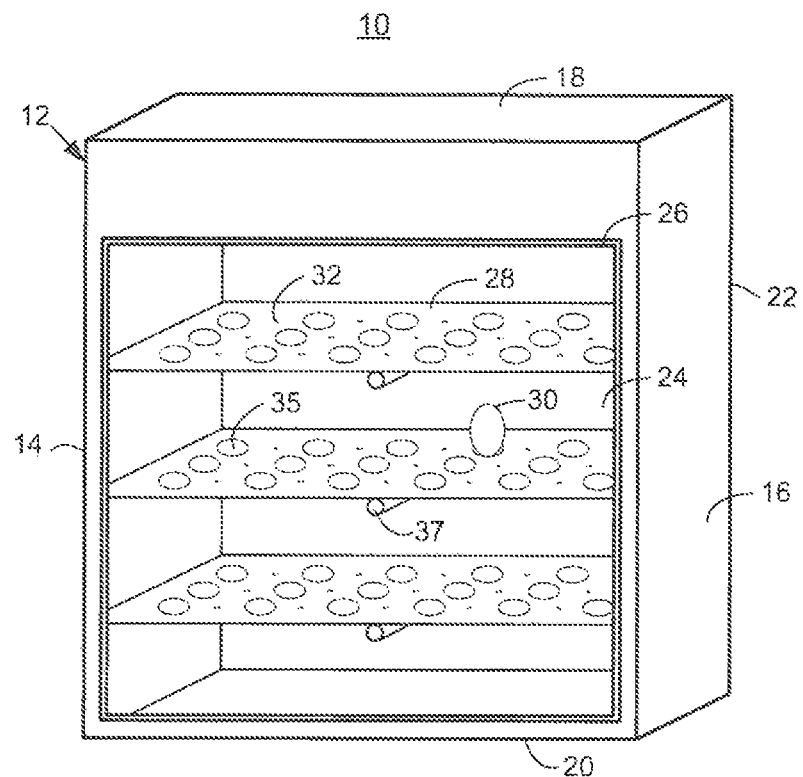
FIGS. 1A, 1B, 1C, 1D, 1E and 1F are schematic diagrams of an incubating device in accordance with the inventive concepts described herein.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The various systems and methods disclosed herein relate to controlling or influencing the sex of embryos in eggs in order to promote the development of embryos of a selected sex.

The systems and methods rely on the application of light having selected wavelengths to incubated eggs in order to influence the sex ratios of embryos in development within the eggs. The systems include an incubating device having an interior cavity in which lighting elements emitting light having the selected wavelengths are mounted. The lighting elements are mounted on trays designed to hold the eggs, such that light emitted by the lighting elements irradiates the eggs. The lighting elements illuminate the eggs during an early incubation period, and thereby promote the production of eggs of a selected sex.

Various studies have been performed on sex-determination in avians. In one study, the localization of P450 (17-alpha) and P450 aromatase (P450arom) mRNA expression was studied in the gonads of chicken embryos at days 4-9. The first detection of P450 (17-alpha) mRNA was at days 5-6 of incubation in the genetic male and female gonads, and the first detection of P450arom at day 6.5 in the female gonad with none in the male gonad. Thus sex determination in chickens appears not to occur until several days after incubation.

Further, estrogen synthesis plays a critical role in avian sex determination. The two terminal enzymes necessary for estrogen synthesis, P-450 aromatase and 17βHSD are expressed only in ZW (female) gonads at the onset of morphological differentiation (day 6-6.5). Aromatase and 17βHSD are therefore the key sexually dimorphic components.

Enzyme synthesis is very sensitive to environmental stimuli. One known environmental stimuli is temperature, as observed in temperature-dependent sex determination (TSD). TSD is a type of environmental sex determination in which the temperatures experienced during embryonic development determine the sex of the offspring. It is most prevalent and common among amniote vertebrates that are classified under the reptile class. For that matter, studies have shown that increased incubation temperature in very specific H&H stages (a series of normal stages in the development of the chick embryo as provided by Hamburger V, Hamilton H L Dev. Dyn. 1992 December, 195(4): 231-272) changes the gender of poultry; however, such increase in temperature causes a decrease in hatchability to the point where such a gender change is not economically beneficial.

Specific wavelengths of light are known to cause photoisomerization such that enzymatic activity can be effectively controlled by wavelength of light. In particular a recent study showed that restriction endonucleases could be used as a molecular scissors to cut the phosphodiester bond to generate a double stranded break. In this manner the catalytic activity of the orthodox restriction endonuclease PvuII by light was provided.

Additionally, research has shown that by using RNA interference to reduce DMRT1 (doublesex-mab-3-related transcription factor 1) protein expression leads to feminization of the embryonic gonads in genetically male embryos causing partial sex reversal. DMRT1 has a zinc finger core which may absorb near UV light (e.g., light having a wavelength of approximately 430 nm, such as light having wavelengths in the 410 nm-430 nm range), and may thereby similarly reduce DMRT1 protein expression. Thus, the resulting lower levels of DMRT1 lead to fewer male offspring and more female offspring.

Reference now is made in detail to the examples illustrated in the accompanying drawings and discussed below.

FIG. 1A show an incubating device 10 that has a body 12. In the illustrative embodiment of FIG. 1A, the body 12 has a generally rectangular cuboid shape having first and second sidewalls 14 and 16 parallel to each other. The first and second sidewalls 14 and 16 are connected to and orthogonal to top and bottom walls 18 and 20 that are themselves in parallel to each other. A back wall 22 defines a hollow interior cavity 24 of the body 12. A front wall or door 26 is hingedly connected to one of the sidewalls 14 and 16 to allow access to the interior cavity 24 of the body 12, while also enabling the interior cavity 24 to be isolated from the outside environment when the door 26 is closed. In some examples, the door 26 is made of a transparent material and/or includes a window to allow a user to view the interior cavity 24 while the door 26 is closed. In other examples, the door 26 completely encloses the interior cavity 24. The door 26 may further be formed of one-way window such that a user can view the interior cavity 24 from outside, while light from outside of the cavity 24 does not enter the cavity 24 through the window. The body 12 generally shields the inside of the incubating device 10 and eggs located in the incubating device 10 from radiation, including light, that is present outside of the incubating device 10.

A plurality of holding members or trays 28 are disposed within the interior cavity 24. The trays 28 are configured to receive and stably hold a plurality of eggs 30. As shown, each tray 28 can include a plurality of slots, holes 35, or other cups each configured to stably hold one egg. The trays 28 are mounted to the interior of the body 12. In some examples, the trays 28 are mounted on one or more actuators that enable the trays 28 to move with respect to the body 12. In one example, each tray 28 is mounted on a rotatable axle 37 mounted to and controlled by a rotational actuator 39 (see FIG. 1B). The actuator 39 is itself mounted to the body 12, and is operative to move the trays 28 with respect to the body 12. The actuator may continuously or periodically move the trays 28 having the eggs 30 disposed thereon. In the one example, the actuator 39 is operative to rotate the tray between a horizontal position (as shown) and angled positions in the clockwise and counter-clockwise directions. The angled positions may correspond to angles measured from the horizontal, and may range between 0° and a maximum angle (e.g., 15° or 30°). The maximum angle is generally selected such that even when the tray is rotated to the maximum angle, any eggs 30 disposed on the tray 28 are not dislodged from their slots, holes 35, or cups.

The eggs 30 can be of any avian species, including, but not limited to chicken eggs, turkey eggs, and the like. Reptilian and other species' eggs may also be used. The trays 28 rotate or tilt to various angles in response to actuators 39 to simulate the movement the egg would encounter in nature, for example as the egg is laid upon by a hen or subject to other environmental conditions.

Figure 1B:
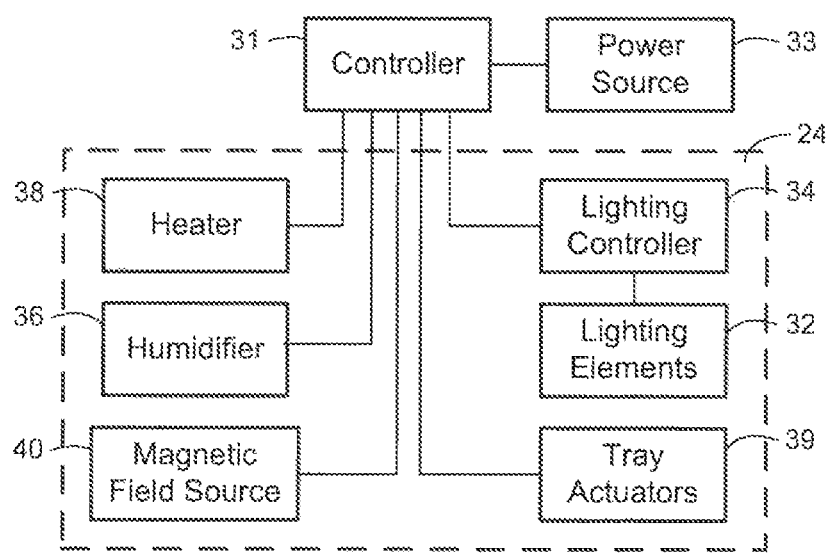
Figure 1C:
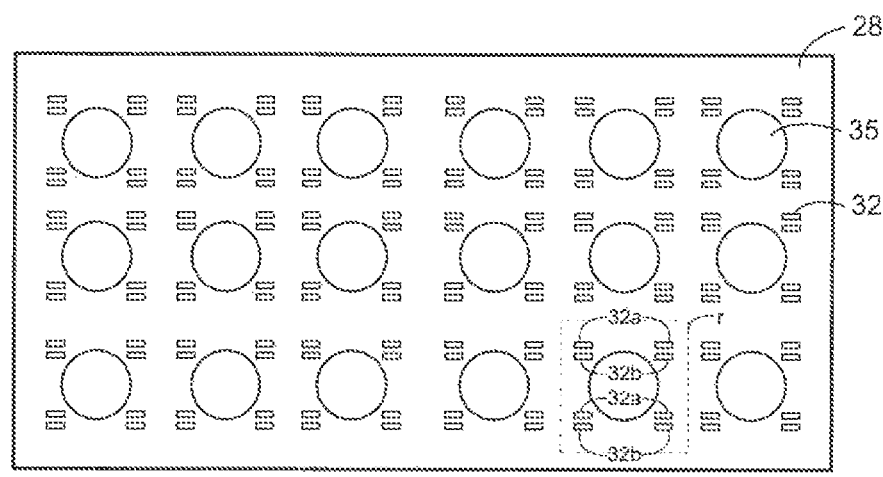
Figure 1D:
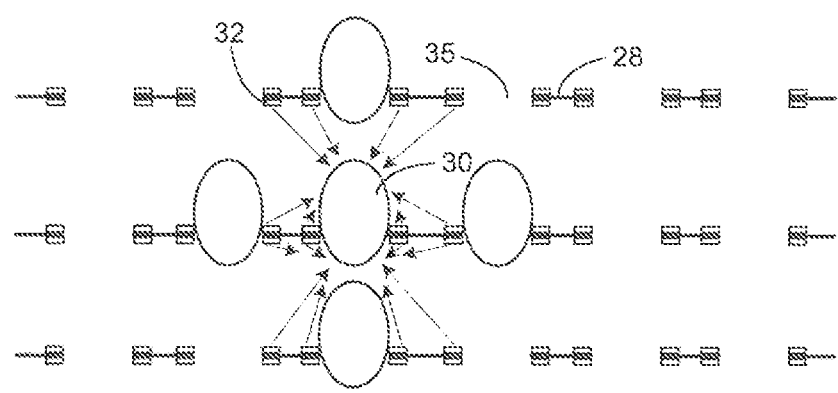

FIG. 1C provides a detailed top view of a tray 28, while FIG. 1D provides a cross-sectional view through multiple trays 28. Note that in some embodiments, the top and bottom views of a tray 28 are substantially identical, and in such embodiments a bottom view of a tray 28 may thus be substantially identical to the view shown in FIG. 1C.

Figure 1E:
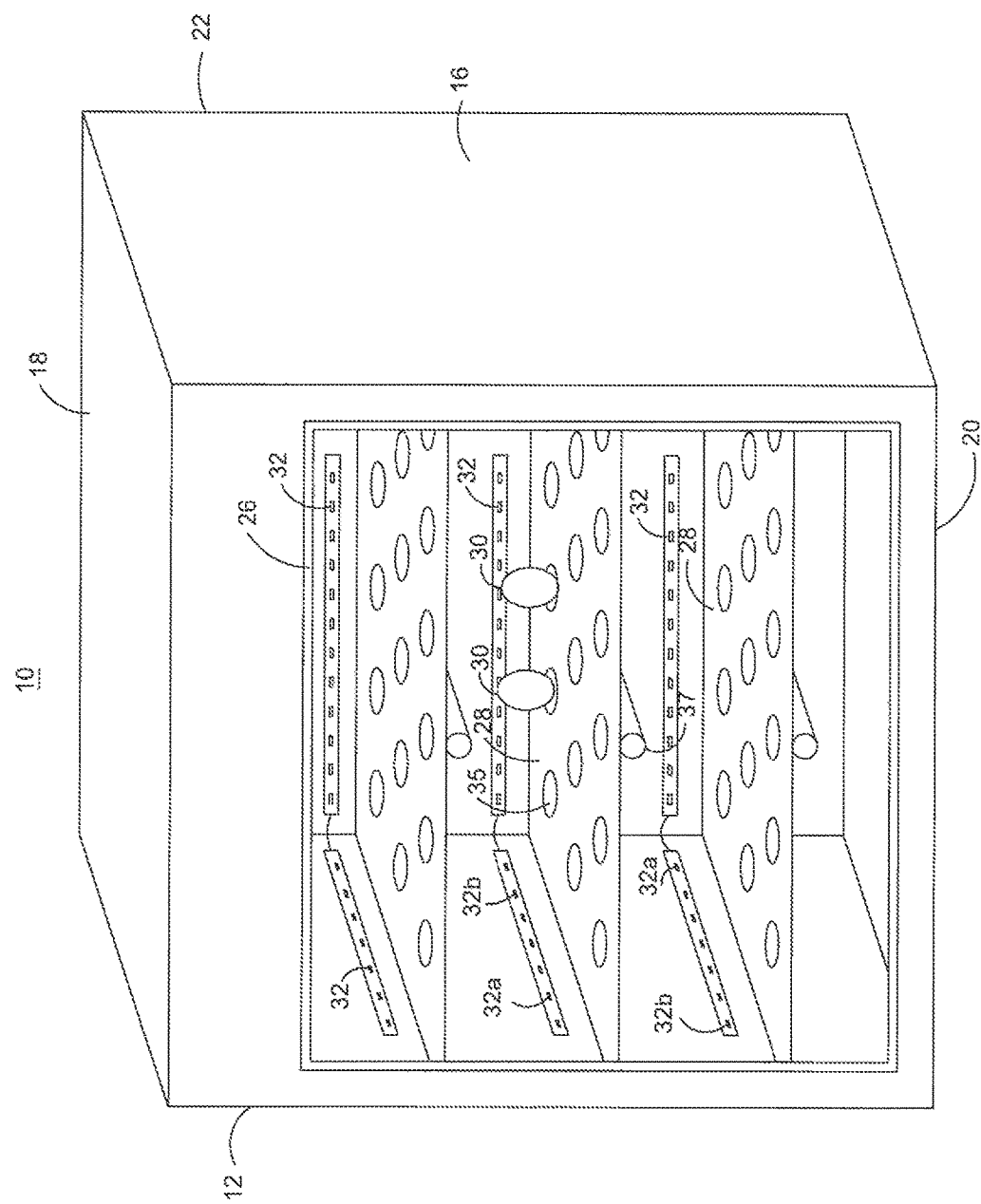
Figure 1F:
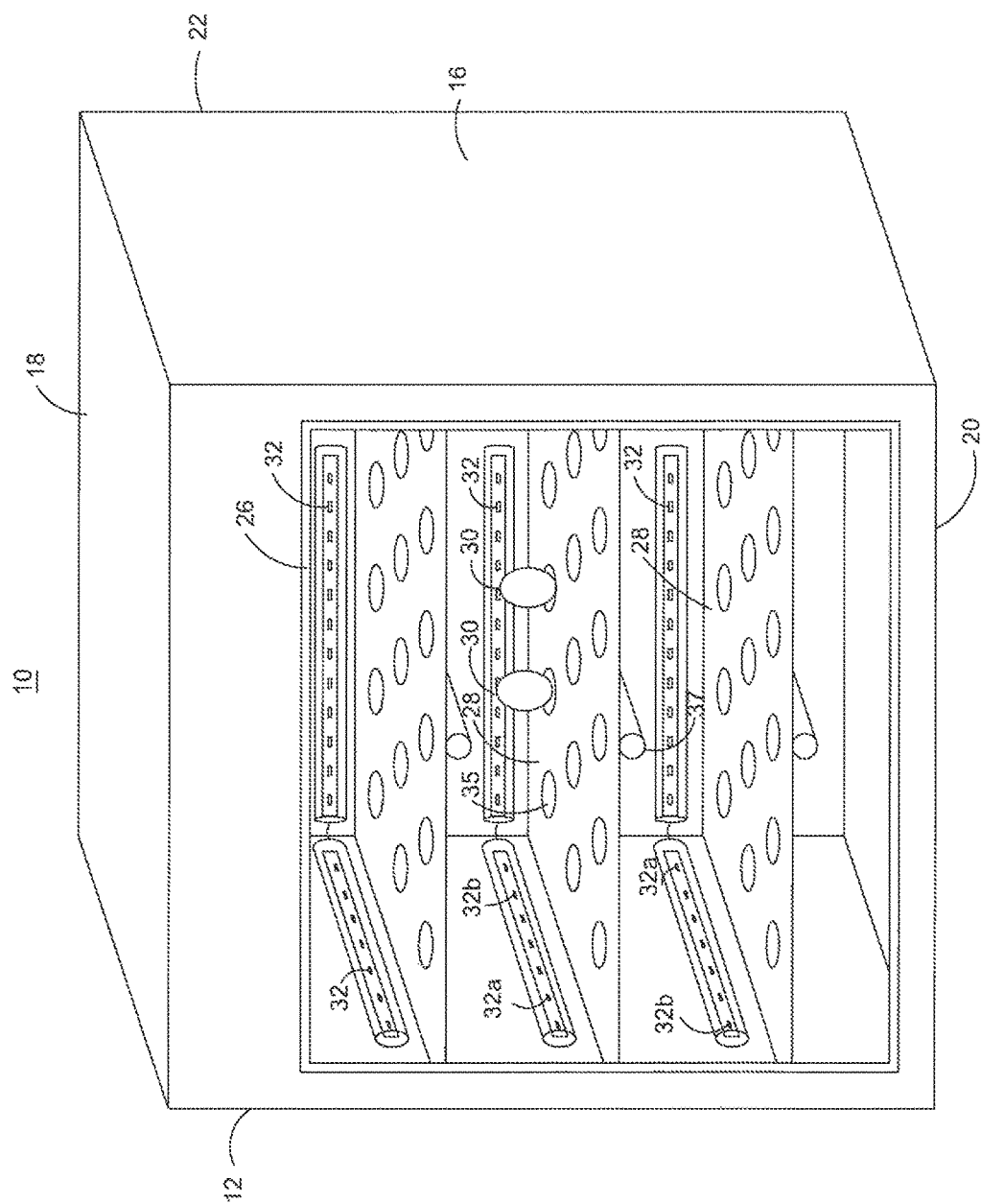

As shown in FIGS. 1C and 1D, a plurality of lighting elements 32 are disposed on one or both surfaces of each tray 28. In one example, the lighting elements 32 are disposed only on an underside of each tray 28. In another example, the lighting elements 32 are disposed only on an upper surface of each tray 28 (corresponding to a surface on which the eggs 30 are disposed). In other examples, the lighting elements 32 are disposed on both the underside and the upper surface of each tray 28, as shown in FIG. 1D. Lighting elements 32 can additionally or alternatively be disposed on surfaces of the body 12 (e.g., surfaces of the interior cavity 24 as provided in FIGS. 1E and 1F), or other locations from which light and/or radiation emitted by the lighting elements 32 reach the eggs 30.

In general, the lighting elements 32 are disposed such that they can provide a high lighting intensity to each egg 30 disposed in the incubating device 10. The lighting elements 32 may thus be disposed in close proximity to the slots, holes 35, or cups holding the eggs 30, as shown in FIGS. 1C and 1D. Further, the lighting elements 32 are disposed such that light emitted by the elements 32 can reach all or substantially all surfaces of each egg 30. Hence, as shown in FIG. 1D, an egg 30 can receive light emitted by the elements 32 from all sides. The trays 28 and of the slits, holes 35, or cups for holding the eggs 30 can also be designed so as to enable substantially all surfaces of each egg 30 to receive light.

The lighting elements 32 are electrically connected to one another and to an electrical power source 33 (shown in FIG. 1B). In a preferred embodiment the plurality of lighting elements 32 are light emitting diode (LED) elements that receive an AC voltage and/or AC current waveform at their terminals for activation. In particular, the assembly formed of the lighting elements 32 and power source 33 can incorporate AC driven LED technology from any one of the following patent applications: U.S. Pat. Pub. No. 2011/0101883 to Grajcar; U.S. Pat. Pub. No. 2011/0109244 to Grajcar; U.S. Pat. Pub. No. 2011/0210678 to Grajcar; U.S. Pat. Pub. No. 2011/0228515 to Grajcar; U.S. Pat. Pub. No. 2011/0241559 to Grajcar; U.S. Pat. Pub. No. 2011/0273098 to Grajcar; U.S. patent application Ser. No. 13/452,332 to Grajcar; and/or U.S. Pat. Prov. Appl. No. 61/570,552 to Grajcar, which are all incorporated in their entirety herein.

The incubating device 10 can include various systems for controlling conditions within the interior cavity 24 of the device 10. FIG. 1B is a block diagram of some systems operative to control environmental and other conditions within the interior cavity 24. As shown in FIG. 1B, the incubating device 10 can thus include a heater 38 and/or cooler for controlling a temperature in the interior cavity 24, and/or a humidifier 36 and/or de-humidifier for controlling a level of moisture in the interior cavity 24. An optional magnetic field source 40 can further be used to apply a constant and/or time-varying magnetic field or flux within the interior cavity 24 in response to an excitation current applied to the source 40. In embodiments including a magnetic field source 40, the walls of the body 12 and/or the interior walls of the cavity 24 may provide magnetic shielding and provide a return path for the magnetic field or flux applied to the cavity 24. Tray actuators 39 may further be mounted to the trays 28 so as to be operative to continually or periodically move, rotate, or shake the trays 28. As noted previously, the incubating device further includes lighting elements 32 configured to emit light and/or other radiation for application to eggs 30 disposed in the interior cavity 24. Each of the systems receives power for operation from power source 33.

A controller 31 is operative to operate the systems operative to control environmental and other conditions within the interior cavity 24. The controller 31 can activate and de-activate each system, and can further regulate the operation of the systems to reach a pre-determined temperature, humidity, magnetic field or flux, or the like. The controller 31 may include or be electrically coupled to sensors (not shown) located in the interior cavity 24 and providing the controller 31 with information on current environmental conditions including temperature, humidity, and the like. In some embodiments, the controller 31 includes a clock and is operative to control the systems according to a pre-determined schedule. The controller 31 may thus operate the systems on a periodic basis (e.g., by repeating an activation pattern each day), or on another time-varying basis (e.g., by activating the systems according to different patterns on each day of incubation).

A lighting controller 34 is operative to control operation of the lighting elements 32. The lighting controller 34 can be separate from the controller 31 (as shown), or the lighting controller 34 can be integrated within the controller 31. The lighting controller 34 is operative to control the intensity and wavelength of light emitted by each lighting element 32. The lighting controller 34 can further activate and/or dim the lighting elements 32 on a continuous or on a time-varying basis (e.g., a periodic or an aperiodic basis), as described in further detail below.

The lighting controller 34 can operate the lighting elements 32 in unison, such that all lighting elements are synchronously activated and de-activated, and/or such that all lighting elements are activated with a same lighting intensity or dimming. Alternatively, the lighting controller 34 can operate different sets of lighting elements 32 differently, for example to cause a first set of lighting elements 32 to be activated for a particular period of time (and/or at a particular intensity level) and cause a second set of lighting elements 32 to be activated for a different period of time (and/or a different intensity level).

In some embodiments, the lighting controller 34 is operative to control a wavelength of light emitted by the lighting elements 32. In particular, the plurality of lighting elements 32 may include multiple sets of lighting elements 32 each operative to produce light having a different wavelength. For example, the plurality of lighting elements 32 can include a first set of lighting elements operative to produce light having a wavelength within a first range of wavelengths (e.g., 410-450 nm, 450-495 nm, or other narrow wavelength range), and a second set of lighting elements operative to produce light having a wavelength within a second range of wavelengths (e.g., 410-450 nm, 450-495 nm, or other narrow wavelength range) different from and non-overlapping with the first range. Note that a light sources is operative to produce light having a spectrum substantially concentrated within the specified range of wavelength (e.g., 410-450 nm, 450-495 nm, or other narrow wavelength range) when over 90% or over 95% of the lighting energy emitted by the light source is within the specified narrow range of wavelengths. In some examples, the light source may thus also emit a small amount of light (e.g., less than 10%, or less than 5% of lighting energy) outside of the specified range. The plurality of lighting elements 32 can further include additional sets of lighting elements operative to produce light having other wavelengths. The lighting controller 34 is operative to control each set of lighting elements 23 separately, and can thereby adjust the range of wavelengths of light that is emitted by the plurality of lighting elements 23 by selectively activating the different sets of lighting elements 23 at respective lighting intensities.

In general, the eggs disposed inside of the incubating device 10 are shielded from light and other radiation that is present outside of the incubating device 10. As a result of the shielding, including the shielding provided by the incubating device 10, the eggs 30 may therefore be only exposed (or substantially only exposed) to the range of wavelengths of light emitted by the lighting elements 23 in the incubating device 10 that are activated during the incubating period. Furthermore, the lighting controller 34 may be operative to ensure that no lighting elements 23 producing light with wavelengths substantially concentrated outside of the specified range are activated during the incubation period, or during the period in which the specified range of wavelengths are applied to the eggs.

For example, in region 'r' of tray 28 shown in FIG. 1C, two different sets of lighting elements 32 are provided: a first set of lighting elements 32a is operative to emit light within one range of wavelengths, while a second set of light elements 32b is operative to emit light within another range of wavelengths. The lighting controller 34 is operative to separately control the sets of lighting elements 32a and 32b such that each set can be activated at a different time and with a different intensity than other sets of lighting elements. Different sets of lighting elements can similarly be provided on the rest of the tray 28 outside of region 'r', including on another surface of tray 28.

In one embodiment, the plurality of lighting element 32 includes lighting elements 32 emitting blue wavelength (450-495 nm) light, ultraviolet light, or electromagnetic radiation. The lighting elements 32 are controlled by lighting controller 34 that is operative to dim the intensity of the light so as to reduce the intensity to less than 3 lumens. Thus, a constant low intensity wavelength light is emitted throughout the interior cavity 24. The light can be of a narrow frequency or monochromatic to direct the exact wavelength of light desired. In addition, while described as low intensity, a higher intensity wavelength of light can be provided if needed by the controller 34. Further, in the embodiment where LED elements are utilized as lighting elements 32 because of the properties of LED lighting elements, the lights can be left on for long durations of time.

In the same or another embodiment, the plurality of lighting elements 32 includes lighting elements 32 emitting light have wavelengths ranging from 410-450 nm. The lighting elements 32 further are controlled by the lighting controller 34 that is operative to dim the intensity of the light so as to reduce the intensity to less than 3 lumens. Thus, a constant low intensity wavelength light is emitted through the interior cavity 24. In addition, while described as low intensity, a higher intensity wavelength of light can be provided if needed by the controller 34.

While the intensity of the light can be reduced to less than 3 lumens, the intensity of the light similarly can be increased to outputs of 800 lumens, 1000 lumens, or more. Similarly, while light duration can be for long periods of time such as days, weeks, or months, the duration between light and dark periods can also be controlled to a precision of hours, minutes, seconds, and even milliseconds by the lighting controller 34.

In other embodiments, the plurality of lighting elements 32 includes on a same tray 28 lighting elements emitting electromagnetic radiation and light in the ultraviolet/blue wavelength range, as well as lighting elements emitting light in the red wavelength range.

The humidifier 36 is also associated with the interior cavity 24 and is preferably attached to the top wall 18. The humidifier 36 has a tubing element that can increase the humidity level within the interior cavity 24 when the door 26 is closed. The humidifier 36 can include a water input port for receiving water. In this manner, the humidity within the interior cavity 24 can be controlled to provide any relative humidity from 0% humidity to 100% humidity, such that the humidity with the interior cavity 24 is pre-determined. Preferably the humidity is maintained within a range of 50%-80% humidity. In some examples, a dehumidifier can also be used to maintain humidity within the pre-determined range.

The heater 38 is also electrically connected to the power source 33, and is disposed within the interior cavity 24 to provide a predetermined amount of heat within the interior cavity. Preferably, the interior cavity 24 of the incubation device 10 is kept at a temperature of between 90 and 110 degrees Fahrenheit during incubation.

In one embodiment, the magnetic field source 40 is associated with the incubating device 10, and is mounted within the interior cavity 24 to form a pre-determined magnetic flux through or affecting eggs 30 disposed in the cavity 24.

Figure 2:
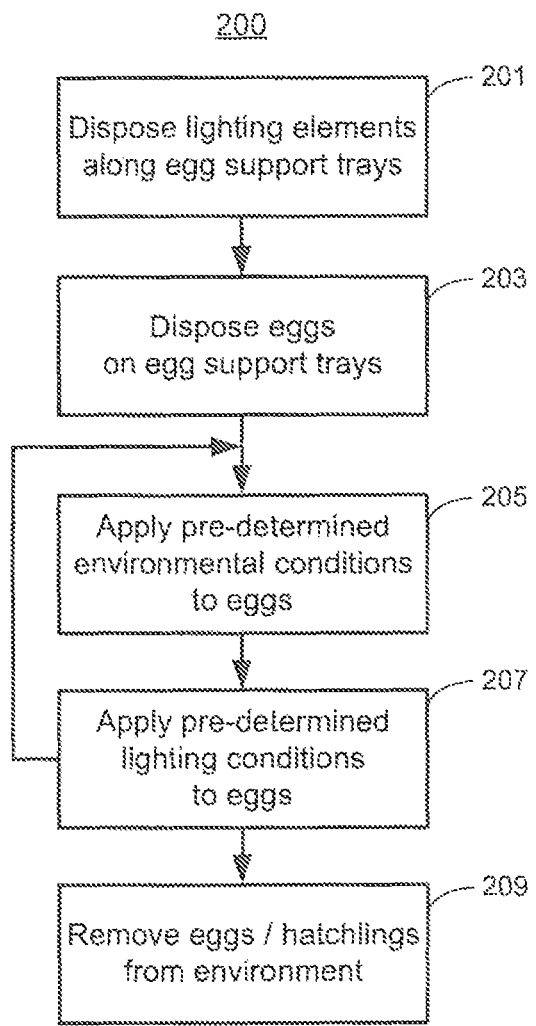
FIG. 2 is a flow diagram showing steps of a method for controlling the sex of oviparous embryos using light sources.

FIG. 2 is a flow diagram showing steps of a method 200 for controlling the sex of oviparous embryos using light sources. The method can be performed using an incubating device such as incubating device 10, or using any other appropriate device.

Method 200 begins with step 201 in which lighting elements (e.g., lighting elements 23, such as LEDs) are disposed along egg support trays. In embodiments in which incubating device 10 is used, the egg support trays are trays 28. Lighting elements can be mounted on the egg support trays as shown in FIGS. 1C and 1D, including on upper and/or lower surfaces of the egg support trays. Alternatively or additionally, lighting elements can be mounted on side surfaces of the interior cavity 24 so as to be disposed along the egg support trays and to illuminate upper and/or lower surfaces of the egg support trays. Lighting elements may emit light within a pre-determined wavelength range, and different sets of lighting elements emitting light in different wavelength ranges may be disposed along the support trays.

In step 203, eggs are disposed on the egg support trays alongside of which the lighting elements have been disposed. In embodiments in which incubating device 10 is used, the eggs 30 are disposed within slits, holes 35, or cups located on or in the trays 28 and configured to hold the eggs 30 in place. The eggs are disposed so as to be spaced apart and evenly distributed on the egg support trays to ensure that light emitted by the lighting elements can reach substantially the entire outer surface of each egg 30.

Once the eggs are in place on the support trays, pre-determined environmental conditions are applied to the eggs in step 205. The environmental conditions can include pre-determined levels of humidity and temperature. The environmental conditions can further include application of a magnetic field. The environmental conditions can additionally include movement or actuation, for example provided by tray actuators 39 operative to rotate trays 28 on rotational axles 37. In general, the environmental conditions are applied according to a pre-determined multi-day schedule, such that different environmental conditions can be applied on different days and/or at different times during each day. The environmental conditions are generally selected to promote hatching of the plurality of eggs.

In addition to environmental conditions, pre-determined lighting conditions are applied to the eggs in step 207 during the application of the environmental conditions. The lighting conditions are selected to promote production of embryos of a selected sex in the eggs. The lighting conditions can include pre-determined wavelengths of light being provided to the eggs 30 by the lighting elements, and pre-determined lighting intensities being provided for each wavelength. The lighting conditions are generally applied according to a multi-day schedule, such that different lighting conditions can be applied on different days and/or at different times during each day in accordance with environmental conditions applied over the multi-day schedule. The lighting conditions can include irradiating the eggs 30 with light having a spectrum substantially concentrated within a specified range of wavelength (e.g., 410-450 nm, 450-495 nm, or other narrow wavelength range), such that over 90% or over 95% of the lighting energy irradiating the eggs is within the specified narrow range of wavelengths. Note that the eggs may also receive a small amount of light (e.g., less than 10%, or less than 5% of lighting energy) outside of the specified range.

Steps 205 and 207 may be repeatedly performed as adjustments to the environmental conditions and/or lighting conditions are determined and applied to the eggs 30. When the incubation period of the eggs disposed on the support trays has expired, the eggs 30 and/or hatchlings from the eggs 30 are removed from the environment in step 209.

In operation, the pre-determining lighting conditions applied to the eggs in step 207 can be selected to control the sex of embryos contained in the eggs 30. For example, when an increase in the percentage of female avian offspring, such as turkeys, is desired from a plurality of eggs 30 or embryos, the eggs or embryos are illuminated by a predetermined electromagnetic radiation, UV, or blue light. Further, a predetermined humidity and magnetic field are also provided within the incubation device 10. As a result, enzymatic activity in the eggs is controlled in a reversible manner.

Specifically, the "P450" of P450 aromatase was derived from its spectral absorption characteristics (Photonic 450 nm). If this molecule absorbs light it has to convert it to another form of energy. The absorbed energy is not used to power a chemical reaction, nor converted to radiation. Thus heat, or possibly electron low to high spin transition must be the byproduct. This causes an enhancement or control of the enzyme converting potential male avian into female avian.

In another embodiment DMRT1 protein expression is reduced to cause sex reversal. Specifically, the eggs 30 are irradiated with near-UV light or blue light (e.g., light having a wavelength of approximately 430 nm, such as light having wavelengths substantially concentrated in the 410 nm-450 nm range) during the first days of incubation (e.g., during days 0-6 of incubation) to thereby reduce DMRT1 protein expression. Thus, the lower levels of DMRT1 in the eggs 30 resulting from the eggs 30 being exposed to the near-UV light or the blue light leads to fewer male offspring and more female offspring developing in the eggs.

In this manner, wavelength of light can be used to control the synthesis of P-450 Aromatase or reduce DMRT1 protein expression and thus control or divert the sex of avian during the fertilization period so that either a larger percentage of female animals or a larger percentage of male animals result from incubation, as compared to a control group of a plurality of eggs that are not illuminated with the electromagnetic radiation, UV, or blue light. In one embodiment, an increase of at least 5% in the ratio of females to males is obtained relative to the ratio found in a control group in which illumination in the specified wavelength range is not applied. In another embodiment, the increase is of at least 10% in the ratio of females to males among the illuminated eggs relative to the ratio observed in control group eggs.

In particular, an experimental test was conducted using both fertilized turkey eggs and fertilized chicken eggs. The eggs were placed in an incubating device such as incubating device 10 having lighting elements 32 disposed on trays 28 surrounding the eggs during the incubation period. Specifically, LED lighting elements producing monochromatic blue light at approximately 450 nm were mounted on the trays and used to illuminate the eggs during the incubation period for approximately the first 84 hours (3.5 days) of incubation. The incubation device 10 was placed in an environment such that only light from the lighting elements 32 of trays 28 reached the eggs, and the eggs were placed in close proximity to the lighting elements 32 within the incubation device. Prior to placement within the incubation device 10, the turkey eggs were stored at temperatures of approximately 40-50° F. for several hours and then brought to room temperature before being placed into the incubating device 10.

In the experimental test, the turkey eggs were first loaded into the incubating device 10 on the first day of incubation and the chicken eggs were added on the second day of incubation. The humidity, incubation temperature in the device 10, and ambient room temperature outside of the device 10 were recorded during each day of incubation. The humidity was kept at approximately 56%, and the incubation temperature at between 98-100° F. The room temperature typically varied between 67° and 73° F., though the room did reach temperatures in the 80°-90° F. range on a few occasions. After approximately three weeks of incubation, the eggs were removed from the incubating device, and the sex of the embryos in the eggs was determined.

During initial testing, the ratio of female turkey embryos to male turkey embryos was determined to be approximately 2:1. In addition, during the initial test, numerous hermaphroditic turkey embryos were discovered. Upon further analysis, the hermaphroditic turkeys were determined to be female, and a ratio of female turkey embryos to male turkey embryos of 3:1 was obtained. This ratio is in sharp contrast to an approximately 1:1 ratio of females to males obtained for incubated turkey eggs according to typical incubation methodologies in which the pre-determined lighting conditions described herein are not applied. In addition, the turkey eggs in the experiment had 100% hatchability, as compared to hatchability levels of around 85% in the industry using typical incubation methodologies, thus showing that application of the blue wavelength light improves hatchability in avians such as turkeys.

For the chicken eggs, a number of the eggs sexed were determined to be hermaphrodites. As evidenced by the 3:1 sex ratio observed among the turkey embryos and by the hermaphroditic chicken embryos, light can be used to control or influence the sex of embryos in eggs notably in avian species. While the experimental test used only blue light, application of other wavelengths of light including but not limited to ultraviolet, green, yellow, orange, red, and infrared light, can also be used to control the sex of embryos in eggs to varying degrees.

According to preferred protocols, the eggs or embryos are illuminated in step 207 with light having a selected wavelength range (e.g., 390-419 nm, 410-450 nm, 420-450 nm, 450-495 nm, or another appropriate range) at least for a period of one hour per day during the first six-and-a-half (6.5) days of incubation. In one embodiment, the embryos are illuminated for at least one hour per day using light having the selected wavelengths during the first three-and-a-half (3.5) or four-and-a-half (4.5) days of the incubation period. Alternatively, the embryos are illuminated with light having the selected wavelength range for twenty-four (24) hours per day on days zero (0) through six-and-a-half (6.5) of incubation. Alternatively, other periods of illumination applied each day (or on another appropriate periodic basis) during the first six-and-a-half day period (6.5) of incubation is contemplated.

While different wavelengths of light can be used to increase the ratio of male-to-female or to increase the ratio of female-to-male avian embryos (as compared to control group ratios), similarly the intensity of light or lumen output applied to eggs can have an effect. Thus, depending on the avian species, whether turkey, chicken, duck, or the like, the exact wavelength and intensity (e.g., amount or number of lumens) can be determined to optimize the increase in the percentage of males or females born from a plurality of eggs when using lighting as compared to the percentage provided in a similar control situation (in which light of the selected wavelengths and intensity is not applied).

Similarly, the systems and methods described herein can be applied to eggs of other oviparous species, including fish, amphibians, reptiles, mammals, and the like. In one embodiment, lighting elements 32 are a plurality of underwater lighting apparatuses similar to those disclosed in U.S. patent application Ser. No. 13/715,904 to Grajcar et al. which is incorporated in full herein. The lighting elements 32 provide different wavelength of light to fish eggs located in their vicinity. The light is received by eggs of underwater life such as salmon, and is used to control the sex of the salmon or other species. In one embodiment, light having a blue wavelength of approximately 450 nm is applied to the eggs and causes an increase in the ratio of females to males as compared to a control group to which such wavelengths of light are not applied. Similarly, in another embodiment, light with wavelengths in the Soret band of visible absorption (from about 390 nm-419 nm) causes an increase in the ratio of males to females, as compared to a control group to which such wavelengths of light are not applied. Other wavelengths of light may similarly be utilized and emitted to optimize effects and to take into account the effect of the light traveling through water.

Thus provided is a method and apparatus of accomplishing the same for controlling the sex of embryos including avian embryos. In particular, through the use of lighting assemblies that preferably are AC driven LED lighting assemblies, different wavelength and intensity light is provided to a plurality of avian embryos. Other influencers can include the exposure of the eggs to predetermined humidity and magnetic properties. As a result, the percentage of either males or females from the plurality of embryos is increased at least 5% as compared to embryos not receiving such wavelength and intensity of light. Thus, for egg laying operations, the ratio of female animals obtained from a plurality of eggs can be increased, maximizing the amount of egg layers obtained from the plurality of eggs. This thereby decreases the number of avians that must be euthanized or lost, increasing efficiencies and maximizing profits.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element. The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The invention claimed is:

1. An incubating device comprising:
   a body having an interior cavity;
   a plurality of trays disposed in the interior cavity and receiving at least one egg for incubation; and
   a plurality of lighting elements positioned to emit light reaching substantially an entire outer surface of the at least one egg,
   wherein said plurality of lighting elements are configured to emit light for irradiating the at least one egg with a spectrum substantially concentrated within a pre-determined narrow wavelength range selected based on a selected sex-ratio being promoted in at least one embryo of the at least one egg wherein the plurality of lighting elements are disposed on an upper surface and an undersurface of at least one of the plurality of trays.

2. The incubating device of claim 1 wherein the pre-determined wavelength range is a 410-450 nm wavelength range.

3. The incubating device of claim 1, wherein the pre-determined wavelength range is a 450-495 nm wavelength range.

4. The incubating device of claim 1, wherein the at least one egg is irradiated with light having the pre-determined wavelength range substantially concentrated within a narrow range of wavelengths.

5. The incubating device of claim 4, wherein the at least one egg is only irradiated with light having the spectrum substantially concentrated within the narrow range of wavelengths while the at least one egg is incubated.

6. The incubating device of claim 4, wherein the irradiating of the at least one egg comprises irradiating the at least one egg with light having an intensity of 3 to 800 lumens while the at least one egg is incubated.

7. The incubating device of claim 4, wherein the narrow range of wavelengths are blue wavelengths.

8. The incubating device of claim 1, wherein the irradiating of the at least one egg comprises irradiating the at least one egg with light having an intensity of 3 lumens or less while the at least one egg is incubated.

9. An incubating device comprising:
a body having an interior cavity;
a plurality of trays disposed in the interior cavity and receiving at least one egg for incubation; and
a plurality of lighting elements positioned to emit light directly reaching substantially an entire outer surface of the at least one egg,
wherein said plurality of lighting elements emit light having a spectrum substantially concentrated within a pre-determined wavelength range for irradiating the at least one egg wherein the plurality of lighting elements are disposed on an upper surface and an undersurface of at least one of the plurality of trays.

10. The incubating device of claim 9 wherein the pre-determined wavelength range is a red wavelength range.

11. The incubating device of claim 9, wherein the pre-determined wavelength range is a 450-495 nm wavelength range.

12. The incubating device of claim 9, wherein the at least one egg is irradiated with light having the pre-determined wavelength range substantially concentrated within a narrow range of wavelengths.

13. The incubating device of claim 12, wherein the at least one egg is only irradiated with light having the spectrum substantially concentrated within the narrow range of wavelengths while the at least one egg is incubated.

14. The incubating device of claim 12, wherein the narrow range of wavelengths are red wavelengths.

15. The incubating device of claim 12, wherein the narrow range of wavelengths are blue wavelengths.

16. The incubating device of claim 9, wherein the irradiating of the at least one egg comprises irradiating the at least one egg with light having an intensity of 3 lumens or less while the at least one egg is incubated.

17. The incubating device of claim 9 wherein the pre-determined wavelength range is a 410-450 nm wavelength range.

* * * * *